US008487004B2

(12) United States Patent
Chen et al.

(10) Patent No.: US 8,487,004 B2
(45) Date of Patent: Jul. 16, 2013

(54) LOCAL TREATMENT OF NEUROFIBROMAS

(75) Inventors: Ruihong Chen, Foster City, CA (US); Allan E. Rubenstein, New York, NY (US); Xiaodong Shen, Foster City, CA (US); Scott Stewart, La Jolla, CA (US); Jin-Chen Yu, Palo Alto, CA (US)

(73) Assignee: Nexgenix Pharmaceuticals, Inc., New York, NY (US)

( * ) Notice: Subject to any disclaimer, the term of this patent is extended or adjusted under 35 U.S.C. 154(b) by 18 days.

(21) Appl. No.: 13/524,590

(22) Filed: Jun. 15, 2012

(65) Prior Publication Data

US 2012/0315298 A1    Dec. 13, 2012

Related U.S. Application Data

(63) Continuation of application No. 11/815,443, filed as application No. PCT/US2006/003588 on Feb. 2, 2006, now Pat. No. 8,211,875.

(60) Provisional application No. 60/649,854, filed on Feb. 2, 2005, provisional application No. 60/669,813, filed on Apr. 7, 2005.

(51) Int. Cl.
*A01N 37/12* (2006.01)
*A01N 37/44* (2006.01)
*A01N 37/10* (2006.01)
*A01N 47/28* (2006.01)
*A61K 31/195* (2006.01)
*A61K 37/17* (2006.01)

(52) U.S. Cl.
USPC .......................................... 514/567; 514/597

(58) Field of Classification Search
None
See application file for complete search history.

(56) References Cited

U.S. PATENT DOCUMENTS

| 6,498,152 B1 | 12/2002 | Wainwright et al. |
| 8,211,875 B2 | 7/2012 | Chen et al. |
| 2002/0119095 A1 | 8/2002 | Gabathuler et al. |
| 2003/0191098 A1* | 10/2003 | D'Amato ...................... 514/171 |
| 2009/0118240 A1 | 5/2009 | Chen et al. |

FOREIGN PATENT DOCUMENTS

| GB | 2398495 A | 8/2004 |
| JP | 8-119865 A | 5/1996 |
| JP | 8-268894 A | 10/1996 |
| JP | 11-509204 A | 8/1999 |
| JP | 2005-97197 A | 4/2005 |
| WO | WO 97/02817 A1 | 1/1997 |
| WO | WO 2006/071966 A2 | 7/2006 |

OTHER PUBLICATIONS

Dorwald, "Preface," Side Reactions in Organic Synthesis: A guide to successful synthesis design, Weinheim: Wiley-VCH, Verlag GmbH & Co. KGaA (2005).
Friederich, "International Search Report," 5 pages, PCT appl. No. PCT/US2006/003588, European Patent Office (mailed Sep. 1, 2006).
Friederich, "Written Opinion of the International Searching Authority," 8 pages, PCT appl. No. PCT/US2006/003588, European Patent Office (mailed Sep. 1, 2006).
Landy et al., "Extended remission of a recurrent median nerve malignant peripheral nerve sheath tumor after multimodal treatment," J. Neurosurg. 103(4):760-763 (2005).
Tozon et al., "Elecrochemotherapy: Potentiation of Local Antitumour Effectiveness of Cisplatin in Dogs and Cats," Anticanc. Res. 21(4A):2483-2488 (2001).
Yan et al., "Farnesyltransferase Inhibitors Block the Neurofibromatosis Type I (NF1) Malignant Phenotype," Canc. Res. 55:3569-3575 (1995).
Zhu and Parada, "The Molecular and Genetic Basis of Neurological Tumours," Nature Rev. Canc. 2:616-626 (2002).

* cited by examiner

*Primary Examiner* — Anna Pagonakis
(74) *Attorney, Agent, or Firm* — Cooley LLP

(57) ABSTRACT

A method for treating a neurofibroma, e.g. dermal neurofibroma, a subdermal neurofibroma, or a superficial plexiform neurofibroma, in a subject in need of such treatment is disclosed. The method comprises locally applying a composition to a neurofibroma either topically or intralesionally. This method does not encompass systemic administration of the composition to the subject to have an effect on the neurofibromas. Compositions useful for such treatments and methods of preparing the compositions are disclosed.

5 Claims, No Drawings

LOCAL TREATMENT OF NEUROFIBROMAS

CROSS-REFERENCE TO RELATED APPLICATIONS

This application is a continuation of U.S. patent application Ser. No. 11/815,443, filed on Jul. 22, 2008, which is a U.S. National Stage application of International Application No.: PCT/US06/003588, filed on Feb. 2, 2006, which claims benefit of U.S. Application Ser. No. 60/649,854, filed on Feb. 2, 2005; and of U.S. Application Ser. No. 60/669,813 filed on Apr. 7, 2005, and all of the disclosures of which are incorporated herein by reference in their entirety.

BACKGROUND OF THE INVENTION

Neurofibromatosis type 1 (NF1) is the most common single gene disorder to affect the human nervous system. It is transmitted genetically in an autosomal dominant manner. NF1 affects approximately 1.5 million people worldwide and there is no racial, ethnic, or geographic predilection for the disorder. NF1 is caused by mutation in the NF1 gene, which produces neurofibromin, a tumor suppressor. A high spontaneous mutation rate (50%) at the NF1 locus insure that the disorder is unlikely to decrease significantly in the population due to genetic screening.

People affected by NF1 are at increased risk for developing a variety of tumors of the nervous system, including dermal, subdermal and plexiform neurofibromas; optic pathway astrocytomas, and malignant peripheral nerve sheath tumors ("MPNST"), and for learning disability, scoliosis and certain forms of leukemia. These tumors may cause disfigurement, nervous system damage and chronic pain. Dermal neurofibromas are the commonest lesion in NF1 and occur in 90% of affected individuals. Dermal neurofibromas are typically small (less than 2 cm in diameter), multiple and first develop during puberty. They are typically high in collagen content, have very low metabolic activity, and, as opposed to plexiform neurofibromas, never undergo malignant degeneration. There has never been a reported case of malignant degeneration in a dermal neurofibroma spontaneously or in patients who have received regional radiotherapy for various malignancies or who have received chemotherapy for malignancy.

Certain patients may develop some of the same disfiguring signs that are associated with Elephant Man's disease, a separate disorder originally thought to be NF1. The only treatment at the present time is surgical removal. However, tumors often cannot be removed without causing major neurologic and/or cosmetic problems, and frequently re-grow. They are not responsive to radiotherapy or to known chemotherapeutic agents.

Cutaneous and subcutaneous neurofibromas may develop at any time in life, but their numbers are usually small before puberty. The total number of neurofibromas seen in adults varies from just a few to thousands. Additional cutaneous and subcutaneous neurofibromas develop throughout life, although the rate of appearance may vary greatly from year to year. Other than an actual cure for the condition, an effective non-surgical treatment for dermal neurofibromas is the single highest priority for the 100,000 people in the U.S. affected by NF1. Dermal neurofibromas cause significant disfigurement, pain, psychological and financial stress and should be considered a major unmet medical need in this population. Development of a local treatment for dermal neurofibromas has not previously been explored because of several factors including the relatively low proliferation index with respect to other tumors, and the fact that the tumors reside slightly deeper in the skin especially when compared to basal and squamous cell carcinomas. This local treatment encompasses both topical treatment and intralesional or intradermal treatment at the site of the neurofibroma. Therefore, although such a local treatment of these dermal neurofibromas would be a valuable treatment for an unmet medical need, work has not been done in this area previously.

SUMMARY OF THE INVENTION

One aspect of this invention is a method for treating a neurofibroma, e.g. dermal neurofibroma, a subdermal neurofibroma, or a superficial plexiform neurofibroma, in a subject in need of such treatment. The method comprises locally applying a composition to a neurofibroma. This method does not encompass systemic administration of the composition to the subject to have an effect on the neurofibromas. The method comprises locally administering a composition to the region of the tumor, wherein the composition comprises (a) at least one agent for abating the negative impact of the neurofibroma on the subject, and optionally (b) a pharmaceutically acceptable excipient that aids in transporting the agent into the tumor where it is preferably maintained for a sufficient period of time to negatively impact the neurofibroma.

The method more specifically comprises topically applying a composition to the surface to the skin in the region of the tumor, wherein the composition comprises (a) at least one agent for abating the negative impact of a neurofibroma on the subject, and optionally (b) a pharmaceutically acceptable topical excipient that aids in transporting the agent across the skin into the tumor and preferably maintains the agent on the skin of the subject for a period of time.

Another aspect of the invention is a composition that is useful for treating a neurofibroma (e.g. dermal neurofibroma, subdermal neurofibroma or superficial plexiform neurofibroma) in a subject. The composition comprises (a) at least one agent for abating the negative impact of the neurofibroma on the subject, and optionally (b) a pharmaceutically acceptable topical excipient that aids in transporting the agent across the skin into the tumor, and preferably maintains the agent on the subject's skin for a period of time. The composition alternatively comprises (a) at least one agent for abating the negative impact of the neurofibroma on the subject, and optionally, (b) a pharmaceutically acceptable carrier suitable for injection.

Still another aspect of the invention is a method of preparing a medicament for topically treating a neurofibroma (e.g. dermal neurofibroma, a subdermal neurofibroma, or a superficial plexiform neurofibroma). The method comprises combining at least one agent for abating the negative impact on the neurofibroma on a subject with a pharmaceutically acceptable topical excipient that aids in transferring the agent across the skin into the tumor and preferably maintains the agent on the skin of the subject for a period of time.

A further aspect of the invention is a method of preparing a medicament for intralesionally injecting a neurofibroma. The method comprises combining at least one agent for abating the negative impact on the neurofibroma on a subject with a pharmaceutically acceptable excipient that aids in delivering intralesionally into the tumor so that the agent contacts the tumor of the subject for a period of time.

Other aspects of the invention may be apparent to one skilled in the art after reading the following detailed description.

DETAILED DESCRIPTION

In carrying out the method of this invention, a composition is applied to the surface of the skin in the region of the tumor.

The composition may be applied in any of the known methods for applying composition. Thus, the composition may be sprayed on, dabbed on, rubbed on, or adhered onto the skin using a patch or the like. In addition, it can be applied to the skin and transported across the skin using a microinjection, electrophoretic, ultrasound, or radiofrequency mechanism. It can be delivered using a delivery system that is viral-based or pneumatic. The agent may be formulated as nanoparticles, dendrimers, or liposomes. The composition may take a form of a powder, liquid solution or suspension, a cream, a lotion, an ointment, a gel, or another composition which allows the composition to be maintained on the skin for a period of time that is sufficient to cause the agent to migrate across the skin and to the tumor.

The composition is applied to the skin in the region of the tumor or intralesionally injected into the tumor. Generally, the tumors are readily apparent and will cause disfigurations on the skin. Thus, the application of the composition will be directly to the surface of the skin that is in the region of the tumor. That region will be anywhere on the skin that will be transported across the skin and into the tumor to cause the active agent in the composition to act on the tumor. Once the composition is applied to the skin, it is maintained on the skin for a period of time which is sufficient to transport the agent across the skin into the tumor to abate the negative impact of a neurofibroma on the subject.

For intralesional injection, there are a variety of "active" drug delivery methods and passive drug delivery (a formulation without or without a penetration enhancer). All the technologies perturb the keratin layer of the epidermis to improve drug delivery, with energy of some type or mechanically. The methods include: iontophoresis; ultrasound, radiofrequency (RF) and micro-needles (dermabrasion). Needle-less injection technology, which is a microneedle attached to a CO2 cartridge which forces drug through the skin can also be used.

Abating the negative impact means that (1) the size of the tumor may stabilize and not increase, (2) the tumor may be reduced in size, or (3) the pain and/or itching associated with the tumor may be reduced. Preferably the size of the tumor is reduced significantly as the disfigurement caused by the neurofibromas is a major disadvantage of the condition. Markers for determining whether a composition is acting to abate the negative impact on a subject include measuring the size of the tumor over a treatment period and interviewing the subject to determine if there is a reduction in the level of pain in the subject. Other markers can be developed such as a proliferation index showing the rate of growth of the tumor, an apoptotic index showing the rate of death of the tumor cells, or vessel density. Other biomarkers which may be apparent to one skilled in the art can also be used to measure the success of the composition of this invention. For example, biomarkers that monitor the activation status of Ras-Raf-MEK-MAPK pathway may be used to measure target inhibition in tumor tissues by the composition of this invention. In most cases, a baseline is established before treatment by measuring the size of the tumor using a calipers or using a MRI imaging technique, or establishing an index for the untreated tumor. Once the baseline is established the treatment can begin and measurements can be taken periodically to determine the success of the treatment.

The agents that are useful as a single agent or as a combination of one or more agents in the composition for applying to the surface of the skin or intralesionally injected into the tumor are those that will abate the negative impact of the neurofibroma on the subject. Preferred agents useful in the present invention are agents that are not carcinogenic. The FDA or IARC Monographs have lists of compounds/agents that are considered to be carcinogenic and not suggest or allowed for human use. Even though, bleomycin is listed below as an agent, it is not desirable as a preferred agent because it is carcinogenic. For example, if Such agents may be a chemotherapeutic agent (e.g., an anti-neoplastic agent, a cytotoxin, or an anti-proliferative agent); a sclerosing agent; an immunomodulator (e.g. an immunoregulator, an immunosuppressant, or an immunostimulant) or an anti-inflammatory agent, such as a nonsteroidal anti-inflammatory drugs (NSAID) or a Cox-1 & 2 inhibitor; an agent that modulates gene transcription, e.g. a HDAC (histone deactylase) inhibitor (e.g. valproic acid, FK228, trapoxin), an angiogenesis inhibitor; an agent that alters the structure, function, localization, or post-translational modification of small GTPases (e.g. farnesyl transferase inhibitors [R115777], isoprenyl cysteine transferase inhibitors (cysmethnil) an agent that acts as a chemopreventative agent such as vitamins, vitamin derivatives, antioxidants, nutritional supplements (e.g. fenretinide, green tea extract containing EGCG); an antifibrotic agent, an agent that targets apoptotic or an anti-apoptotic signaling, a kinase inhibitor (e.g. a protein kinase inhibitor or lipid kinase inhibitor); an alkylphospholipid; a protein chaperone inhibitor, such as a heat shock protein inhibitor (e.g., HSP90); an antifungal agent; an agent that restores the function of a mutated gene, such as an agent that suppresses non-sense mutations (e.g., gentamicin); a nucleic acid-based therapeutic agent, a phosphatase inhibitor, a protease inhibitor an or an agent that inhibits skin hyperplasia (e.g., actinic keratosis, melanoma, Kaposi's sarcoma, basal cell or squamous call carcinomas, or skin metastases of other cancers). For topical treatment, the composition preferably contains a skin penetrant that aids in pushing the agent across the skin into the tumor.

Examples of chemotherapeutic agents that are useful are (1) agents that interfere with DNA replication by topoisomerase inhibition, (2) agents that disrupt the microtubule and/or mitotic spindle, (3) agents that act as alkylating or damaging agents to DNA, or (4) agents that interfere with nucleotide synthesis, i.e., antimetabolites. Specific chemotherapeutic agents include 5-fluorouracil (5-FU) and thiotepa. Each of these materials is well known by one of ordinary skill in the art and can be obtained from standard sources.

Protein kinase inhibitors are compounds that target kinases that are hyperactivated in neurofibromas, such as components of the Ras-activated mitogen activated protein kinase pathway (e.g. MEK and Raf kinases), receptor and non-receptor tyrosine kinases, and the AKT-mTOR pathway, which promote cell proliferation and survival, respectively. Lipid kinase inhibitors are compounds that target the phosphatidylinositol 3-kinase pathway, which is hyperactivated in neurofibromas and leads to enhanced cell survival.

Protein chaperone inhibitors are those that inhibit Heat Shock Protein or peptidyl-prolyl isomerase function. Heat Shock Protein activity is required to maintain physiological protein levels of Raf and KSR, two components of the Ras-Mitogen activated protein kinase pathway, in addition to numerous other signaling molecules.

Angiogenesis inhibitors are those that block (1) angiogenesis signaling cascade, such as Vascular Endothelial Growth Factor (VEGF) Receptor signaling, (2) extracellular matrix breakdown, such as that induced by the matrix metalloproteinases (e.g., halofuginone), (3) growth, survival, and migration of endothelial cells, or (4) unknown mechanism of action. Some of these compounds also fall under other categories. These angiogenic processes, among others, are needed to ensure adequate blood supply to a growing tumor and are attractive modes of therapeutic intervention for NF1.

Cell-cell communication, both chemical and physical, between numerous cell types, including Schwann cells, mast cells, and fibroblasts is likely to be essential for neurofibroma disease progression. Immunomodulators, such as calcineurin inhibitors that block transcription of cytokines and growth factors, are an efficient means to interfere with cell-cell signaling.

Agents which correct a specific mutation, such as gene replacement or gentamicin for repair of nonsense mutations, are also useful.

The present invention is more specifically described by the following preferred embodiments:

1. A method of treating a dermal neurofibroma, a subdermal neurofibroma, or a superficial plexiform neurofibroma in a subject in need of such treatment, which method comprises locally administering a composition to the region of the tumor, wherein the composition comprises (a) at least one agent for abating the negative impact of the neurofibroma on the subject, and optionally (b) a pharmaceutically acceptable excipient that aids in transporting the agent into the tumor where it is preferably maintained for a sufficient period of time to negatively impact the neurofibroma. 2. The method of 1, wherein said local administration is topically applying said composition to the surface of the skin in the region of the tumor, and wherein said excipient aids in transporting the agent across the skin and to the tumor and preferably maintains the agent on the skin of the subject. 3. The method of 1, wherein said local administration is intralesionally injecting said composition into the tumor. 4. The method of any one of 1-3, wherein the agent comprises a chemotherapeutic agent, wherein (1) the agent interferes with DNA replication by topoisomerase inhibition; (2) the agent disrupts the microtubule and/or mitotic spindle; (3) the agent acts as an alkylating or damaging agent to DNA; (4) the agent interferes with nucleotide synthesis or a combination thereof. 5. The method of any one of 1-3, wherein the agent comprises a sclerosing agent. 6. The method of any one of 1-3, wherein the agent is an immunomodulator, an immunoregulator, an immunosuppressant, an immunostimulant, or an non-steroidal anti-inflammatory agent. 7. The method of any one of 1-3, wherein the agent modulates gene transcription. The method of any one of 1-3, wherein the agent is an angiogenesis inhibitor. 9. The method of any one of 1-3, wherein the agent alters the structure, function, localization, or post-translational modification of small GTPases. 10. The method of any one of 1-3, wherein the agent is a chemopreventative agent. 11. The method of any one of 1-3, wherein the agent is an inhibitor selected from the group consisting of a protein kinase inhibitor, a lipid kinase inhibitor, a heat shock protein inhibitor, a protein chaperone inhibitor, a phosphatase inhibitor or a protease inhibitor. 12. The method of any one of 1-3, wherein the agent is an anti-fibrotic agent. 13. The method of any one of 1-3, wherein the agent is an alkylphospholipid. 14. The method of any one of 1-3, wherein the agent targets apoptotic or anti-apoptotic signaling. 15. The method of any one of 1-3, wherein the agent is a nucleic acid-based therapeutic agent. 16. The method of any one of 1-3, where the agent restores the function of a mutated gene. 17. The method of any one of 1-3, wherein the agent inhibits skin hyperplasia. 18. The method of any one of 1-3, wherein the agent is an alkylating agent, such as thiotepa or carboplatin; an anti-metabolite or a nucleoside analogue, such as 5-fluorouracil, triciribine, sangivamycin, or tubercidin; a topoisomerase inhibitor, such as podophyllotoxin; a microtubule inhibitor, such as mebendazole, a sclerosing agent, such as bleomycin, doxycycline or analogues thereof; an anti-inflammatory agent or a nonsteroidal anti-inflammatory agent (NSAID), such as diclofenac; an agent that modulates gene transcription, such as a HDAC inhibitor comprising tricostatin A or valproic acid; a chemopreventative agent, such as a retinoid, such as fenretinide; an alkylphospholipid, such as miltefosine; a HSP90 inhibitor, such as geldanamycin derivatives, such as 17-AAG, radicicol or analogues thereof; halofuginone, gentamicin, rapamycin, or a combination thereof. 19. The method of 1-18, wherein the excipient includes a skin penetrant.

Also disclosed are preferred compositions useful for treatment of neurofibromas. 20. A composition useful for treating a dermal neurofribroma, a subdermal neurofibroma, or a superficial plexiform neurofibroma in a subject, which composition comprises (a) at least one agent for abating the negative impact of the neurofribroma on the subject, and optionally (b) a pharmaceutically acceptable topical excipient that aids in transporting the agent across the skin into the tumor and preferably maintains the agent on the subject's skin for a period of time. 21. The composition of 20, wherein the agent is a chemotherapeutic agent, wherein (1) the agent interferes with DNA replication by topoisomerase inhibition; (2) the agent disrupts the microtubule and/or mitotic spindle; (3) the agent acts as an alkylating or damaging agent to DNA; (4) the agent interferes with nucleotide synthesis or a combination thereof. 22. The composition of 20, wherein the agent comprises a sclerosing agent. 23. The composition of 20, wherein the agent is an immunomodulator, an immunoregulator, an immunosuppressant, an immunostimulant, or an non-steroidal anti-inflammatory agent. 24. The composition of 20, wherein the agent modulates gene transcription. 25. The composition of 20, wherein the agent is an angiogenesis inhibitor. 26. The composition of 20, wherein the agent alters the structure, function, localization, or post-translational modification of small GTPases. 27. The composition of 20, wherein the agent is a chemopreventative agent. 28 The composition of 20, wherein the agent is an inhibitor selected from the group consisting of a protein kinase inhibitor, a lipid kinase inhibitor, a heat shock protein inhibitor, a protein chaperone inhibitor, a phosphatase inhibitor or a protease inhibitor. 29. The composition of 20, wherein the agent is an anti-fibrotic agent. 30. The composition of 20, wherein the agent is an alkylphospholipid. 31. The composition of 20, wherein the agent targets apoptotic or anti-apoptotic signaling. 32. The composition of 20, wherein the agent is a nucleic acid-based therapeutic agent. 33. The composition of 20, where the agent restores the function of a mutated gene. 34. The composition of 20, wherein the agent inhibits skin hyperplasia. 35. The composition of 20, wherein the agent is an alkylating agent, such as thiotepa or carboplatin; an anti-metabolite or a nucleoside analogue, such as 5-fluorouracil, triciribine, sangivamycin, or tubercidin; a topoisomerase inhibitor, such as podophyllotoxin; a microtubule inhibitor, such as mebendazole, a sclerosing agent, such as bleomycin, doxycycline or analogues thereof; an anti-inflammatory agent or a nonsteroidal anti-inflammatory agent (NSAID), such as diclofenac; an agent that modulates gene transcription, such as a HDAC inhibitor comprising tricostatin A or valproic acid; a chemopreventative agent, such as a retinoid, such as fenretinide; an alkylphospholipid, such as miltefosine; a HSP90 inhibitor, such as geldanamycin derivatives, such as 17-AAG, radicicol or analogues thereof; halofuginone, gentamicin, rapamycin, or a combination thereof. 36. The composition of 20-36, wherein the excipient includes a skin penetrant. 37. Use of the composition of any one of 20-36 for the preparation of a pharmaceutical composition for the treatment of neurofibromas in a subject. 38. A method of preparing a medicament comprising the composition of any one of 20-36 for topically treating a dermal neurofibroma, a subdermal neurofibroma, or a superficial plexiform neurofibroma, which method comprises combining at least one agent for abating the negative impact of the neurofibroma on the subject with a pharmaceutically acceptable topical excipient that aids in transporting the agent(s) across the skin into the tumor and preferably maintains the agent(s) on the skin of the subject for a period of time.

Examples of specific compounds alone or in combination that are useful in this invention as an agent for abating the negative impact of a neurofibroma on a subject include thiotepa, doxycycline, bleomycin, diclofenac, carboplatin, 5-fluorouracil (5-FU), mebendazole, halfuginone, gentamycin, rapamycin, miltefosine, and the like.

Further, the agent(s) contained in the compositions either as the single pharmaceutically active agent or in combination with one or more pharmaceutically active agents with or without a pharmaceutically acceptable topical excipient for abating the negative impact of the neurofibroma on a subject, includes but are not limited to the following agents:

1. Chemotherapeutic agents, such as cytotoxins, anti-neoplastic or anti-proliferative agents, for example: agents such as:

An alkylating agent, such as Thiotepa,

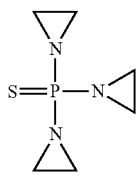 [SMILES: S=P(N1CC1)(N1CC1)N1CC1]

A topoisomerase inhibitor, such as Camptothecin,

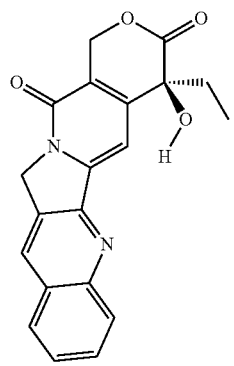 [SMILES: CC[C@@]1(O)C(=O)OCc2c1cc1n(c2=O)Cc2cc3ccccc3nc2-1]

Carboplatin,

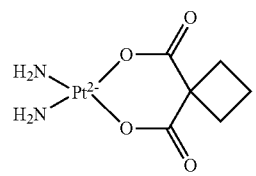

An antimetabolite, such as 5-fluorouracil (5-FU)

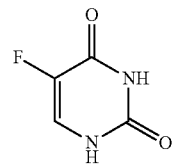

A topoisomerase inhibitor, such as Podophyllotoxin,

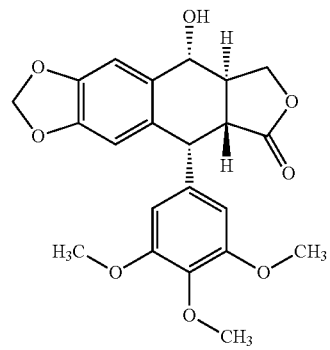 [SMILES: COc1cc([C@@H]2c3cc4c(cc3[C@H](O)[C@H]3COC(=O)[C@H]23)OCO4)cc(OC)c1OC]

A microtubule inhibitor, such as Mebendazole,

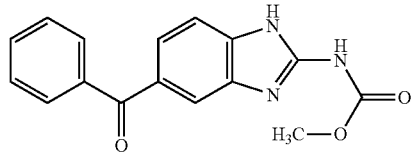 [SMILES: COC(=O)Nc1nc2cc(C(=O)c3ccccc3)ccc2[nH]1]

An antimetabolite or a nucleoside analogue, such as Cladribine

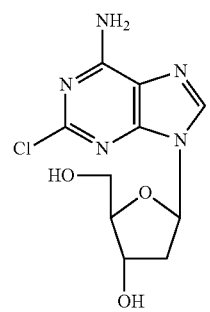 [SMILES: Nc1nc(Cl)nc2c1ncn2C1CC(O)C(CO)O1]

A topoisomerase inhibitor, such as XK469 (2-(4-((7-Chloro-2-quinoxalinyl)oxy)-phenoxy)propionic acid),

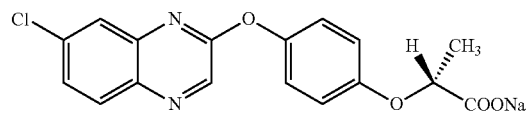

A nucleoside analogue, such as Sangivamycin

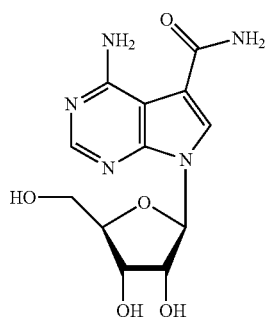

A nucleoside analogue, such as Tubercidin,

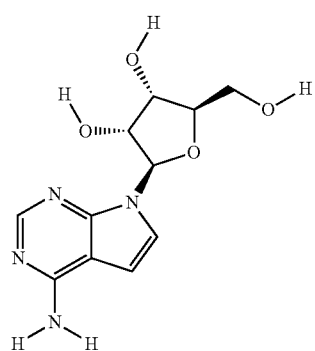 [SMILES: Nc1ncnc2c1ccn2[C@@H]1O[C@H](CO)[C@@H](O)[C@H]1O]

2. Sclerosing agents, for example:

Bleomycin, an antineoplastic antibiotic,

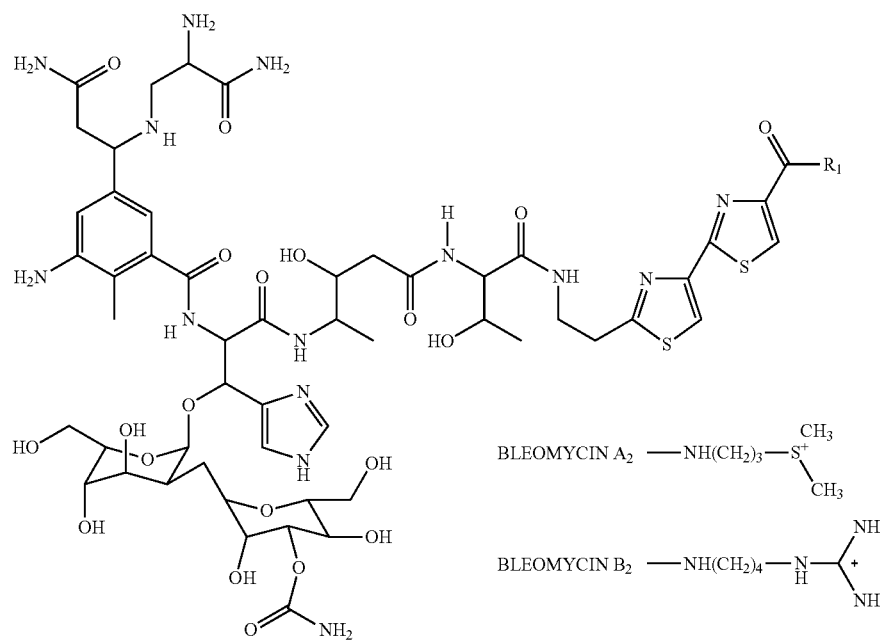

A tetracycline analogue or antibiotic, such as Doxycycline

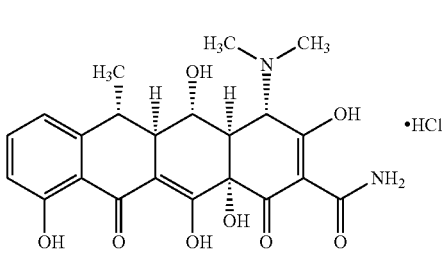 [SMILES: C[C@H]1c2cccc(O)c2C(=O)C2=C(O)[C@]3(O)C(=O)C(C(N)=O)=C(O)[C@@H](N(C)C)[C@@H]3[C@@H](O)[C@@H]21 ; Cl]

3. Immunomodulators or immunoregulators or immuno stimulants or immunosuppressants, for example:

Immunostimulants, such as Imiquimod (immune response modifier or TLR7/8 ligand or agonist),

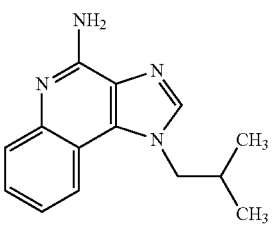 [SMILES: CC(C)Cn1cnc2c(N)nc3ccccc3c21]

Immunosuppressants, such as Tacrolimus (FK506)

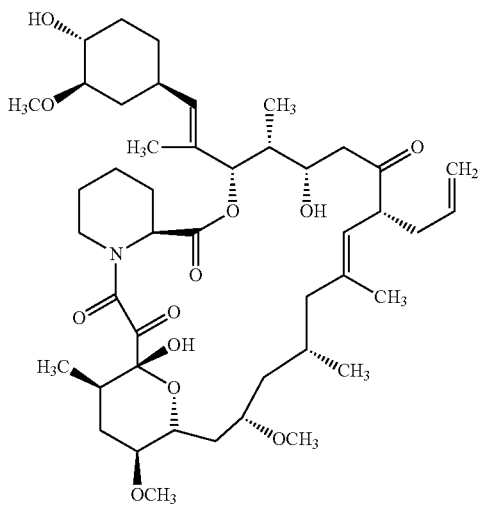

4. An anti-inflammatory agent or non-steroidal anti-inflammatory drug (NSAID), such as:
Diclofenac

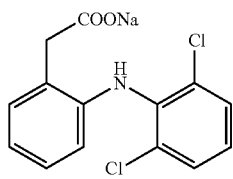

Celecoxib (also a Cox-1 & 2 inhibitor or an anti-inflammatory agent),

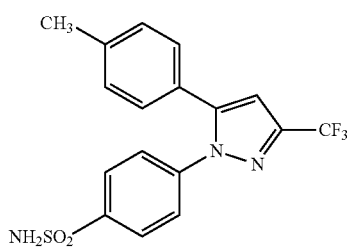

5. Agents that modulate gene transcription; e.g. HDAC (histone deactylase) inhibitors, for example:
A fatty acid class of HDAC inhibitors, such as Valproic acid,

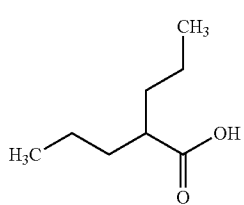

A hydroxamic acid class of HDAC inhibitors, such as Tricostatin A (TSA)

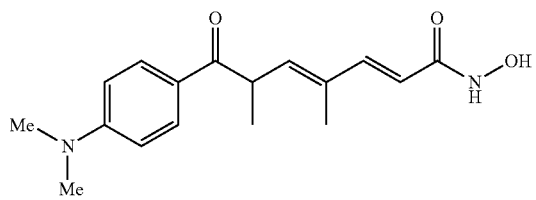 [SMILES: CC(/C=C/C(=O)NO)=C\C(C)C(=O)c1ccc(N(C)C)cc1]

Carbamazepine (below) and its derivatives such as carbamazepine epoxide,

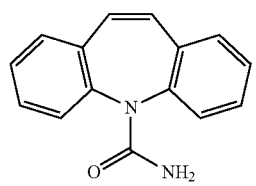 [SMILES: NC(=O)N1c2ccccc2C=Cc2ccccc21]

A cyclic tetrapeptide class of HDAC inhibitors, such as depsipeptide FK228 (FR901228),

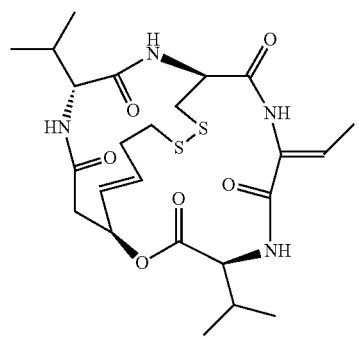 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

6. Angiogenesis inhibitors, for example:
A fumagillin, which is secreted by the fungus *Aspergillus fumigatus*, and its analogues such as TNP-470 [O-(Chloroacetylcarbamoyl) fumagillol] shown below:

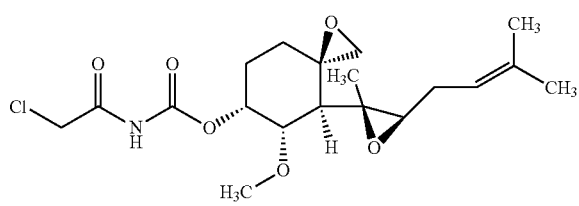 [SMILES: CO[C@@H]1[C@H](OC(=O)NC(=O)CCl)CC[C@]2(CO2)[C@H]1[C@@]1(C)O[C@@H]1CC=C(C)C]

Thalidomide, also an immunomodulatory agent

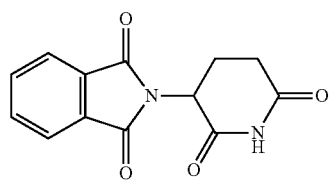 [SMILES: O=C1CCC(N2C(=O)c3ccccc3C2=O)C(=O)N1]

7. Agents that inhibit the cellular process that required for the modification of small GTPases such as:
    Farnesyl transferase inhibitors [e.g. R115777, (B)-6-[amino(4-chlorophenyl)(1-methyl-1H-imidazol-5-yl)methyl]-4-(3-chlorophenyl)-1-methyl-2(1H)-quinolinone],

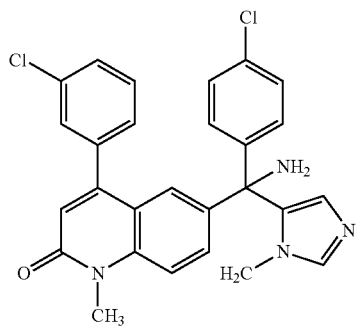 [SMILES: Cn1cncc1C(N)(c1ccc(Cl)cc1)c1ccc2c(c1)c(-c1cccc(Cl)c1)cc(=O)n2C]

Isoprenyl cysteine transferase inhibitors [e.g. cysmethnil]

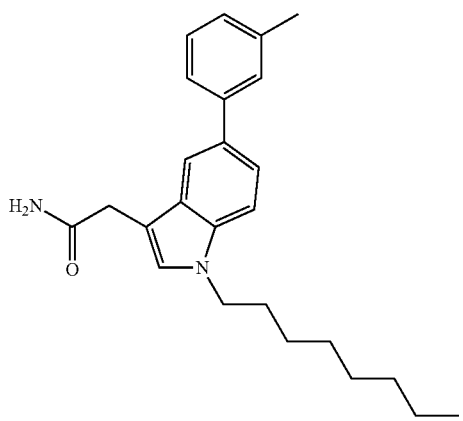 [SMILES: CCCCCCCCn1cc(CC(N)=O)c2cc(-c3cccc(C)c3)ccc21]

HMG-CoA inhibitors (statins, e.g. lovastatin)

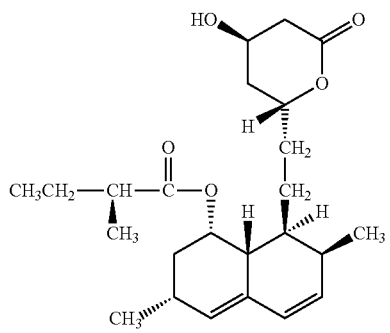

Bisphosphonates (e.g. alendronate, as inhibitors of mevalonate pathway)

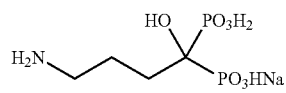

8. Chemopreventative agents, for example:
    Synthetic retinoids (Fenretinide)

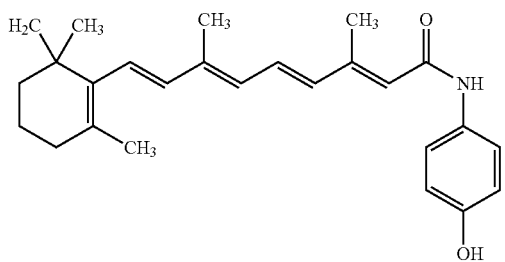 [SMILES: CC1=C(/C=C/C(C)=C/C=C/C(C)=C/C(=O)Nc2ccc(O)cc2)C(C)(C)CCC1]

Retinoic acid [3,7-dimethyl-9-(2,6,6-trimethyl-1-cyclohexenyl)-nona-2,4,6,8-tetraenoic acid] and analogs,

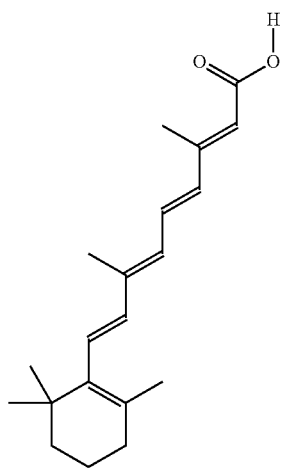 [SMILES: CC1=C(/C=C/C(C)=C/C=C/C(C)=C/C(=O)O)C(C)(C)CCC1]

Curcumin and derivatives,

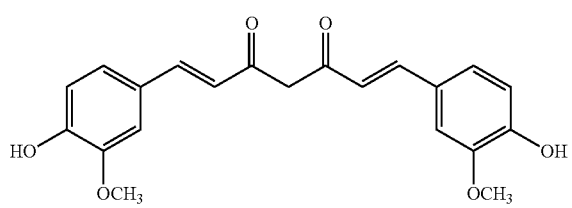 [SMILES: COc1cc(/C=C/C(=O)CC(=O)/C=C/c2ccc(O)c(OC)c2)ccc1O]

EGCG, (−)-Epigallocatechin Gallate (see below) and analogues

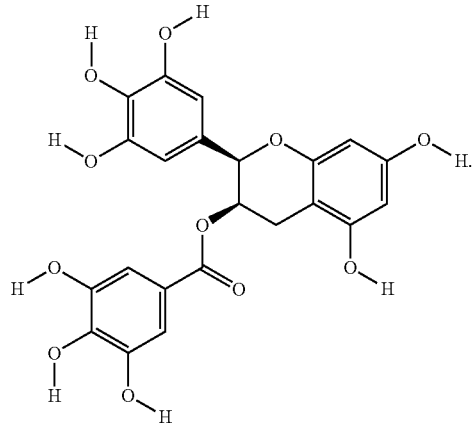

I3C (Indole-3-carbinol),

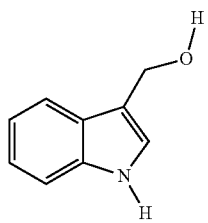 [SMILES: OCc1c[nH]c2ccccc12]

Cyclopamine,

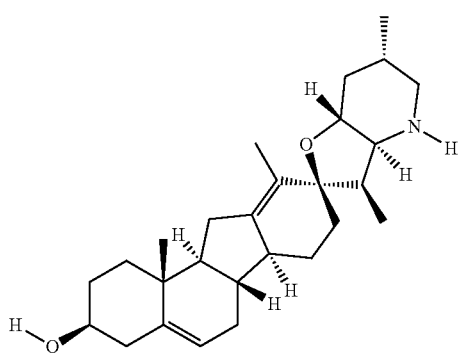 [SMILES: CC1=C2C[C@H]3[C@@H](CC=C4C[C@@H](O)CC[C@@]43C)[C@@H]2CC[C@]12O[C@@H]1C[C@H](C)CN[C@H]1[C@H]2C]

Methylglyoxal,

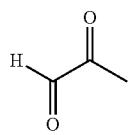

9. Kinase inhibitors, MEK inhibitors, Raf inhibitors, mTOR inhibitors, PI3K inhibitors, examples, such as: MEK inhibitors, such as U0126 [1,4-Diamino-2,3-dicyano-1,4-bis(2-aminophenylthio)-butadiene],

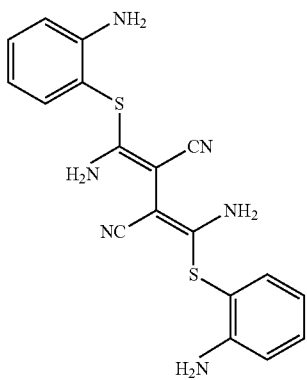 [SMILES: N#CC(=C(/N)Sc1ccccc1N)/C(C#N)=C(\N)Sc1ccccc1N]

PI3K inhibitors, such as Ly294002 [2-(4-Morpholinyl)-8-phenyl-4H-1-benzopyran-4-one]

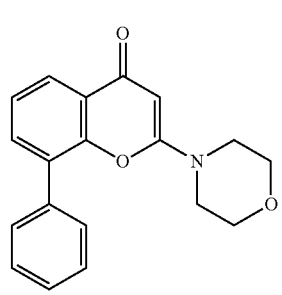 [SMILES: O=c1cc(N2CCOCC2)oc2c(-c3ccccc3)cccc12]

EGFR/ErbB2 inhibitors, such as 4-(4-Benzyloxyanilino)-6,7-dimethoxyquinazoline,

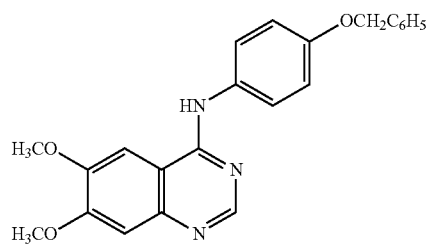

AG1478 (EGFR inhibitor), 4-(3-Chloroanillino)-6,7-dimethoxyquinazoline

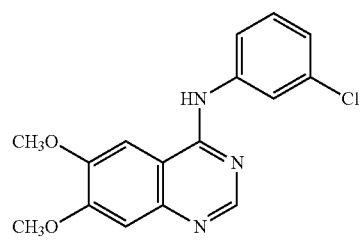

Inhibitors of multiple Tyrosine kinases, e.g. PDGFR inhibitors such as KN2941 (4-(6.7-dimethoxy-4-quinazolinyl)-N-(3,4-methylenedioxybenzyl)-1-piperazinethiocarboxamide)

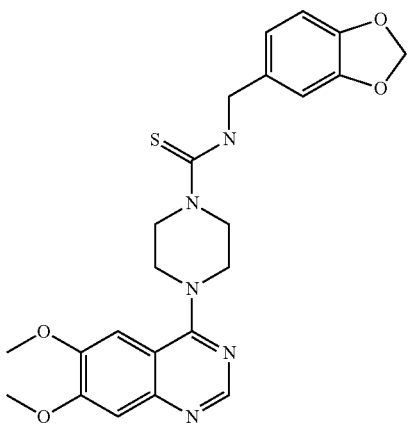 [SMILES: COc1cc2ncnc(N3CCN(C(=S)NCc4ccc5c(c4)OCO5)CC3)c2cc1OC]

Inhibitors of multiple kinases such as SU11652, 5-[(Z)-(5-Chloro-2-oxo-1,2-dihydro-3H-indol-3-ylidene)methyl]-N-[2-(diethylamino)ethyl]-2,4-dimethyl-1H-pyrrole-3-carboxamide

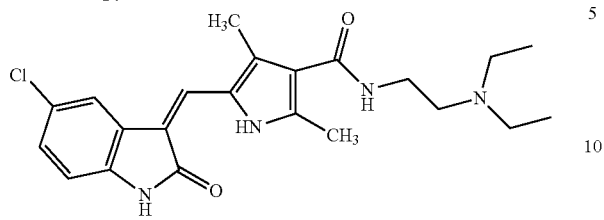

Inhibitors of multiple kinases such as SU11248 (Trade name is Sutent), 5-[(Z)-(5-Fluoro-2-oxo-1,2-dihydro-3H-indol-3-ylidene)methyl]-N-[2-(diethylamino)ethyl]-2,4-dimethyl-1H-pyrrole-3-carboxamide

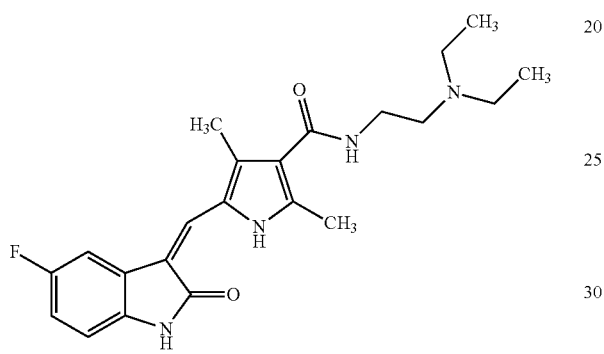

Inhibitors of multiple kinases e.g. VEGFR2 and Raf kinases such as Bay43-9006 (NEXAVAR, or Sorafenib), 4-(4-{3-[4-Chloro-3-(trifluoromethyl)phenyl]ureido}phenoxy)-N2-methylpyridine-2-carboxamide

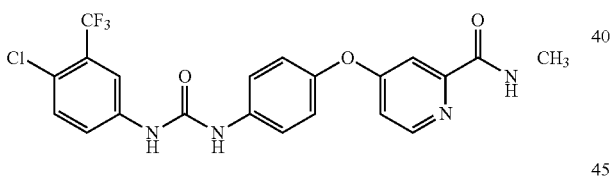

mTOR inhibitors, such as Rapamycin (also an immunosuppressant, see below) and prodrugs or analogue,

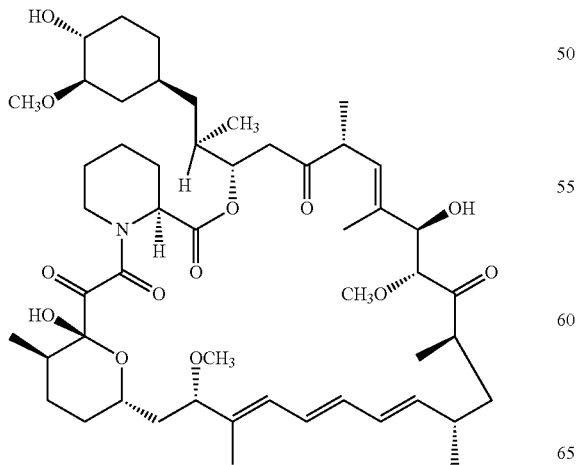

Rho kinase inhibitors such as Fasudil, [1-(5-Isoquinolinesulfonyl)homopiperazine]

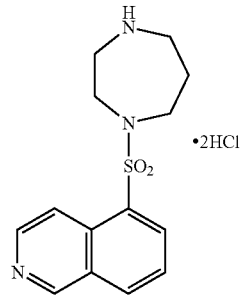 [SMILES: O=S(=O)(c1cccc2cnccc12)N1CCCNCC1]

10. Novel antifibrotics, which may include agents that are also angiogenesis inhibitors, for example:
Halofuginone hydrobromide [(+/−)-trans-7-Bromo-6-chloro-3-[3-(3-hydroxy-2-piperidinyl)-2-oxopropyl]-4(3H)-quinazolinone hydrobromide]

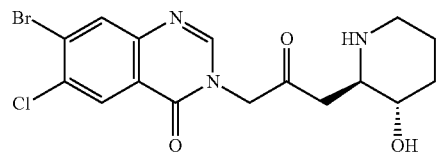 [SMILES: O=C(C[C@H]1NCCC[C@@H]1O)Cn1cnc2cc(Br)c(Cl)cc2c1=O]

Pirfenidone (5-Methyl-N-phenyl-2-1H-pyridone-d5)

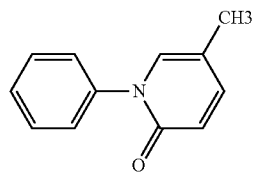

11. Alkylphospholipids, for example:
A. Miltefosine (HePC)
B. Edelfosine (Et-18-OCH3)
C. Perifosine (D21266)

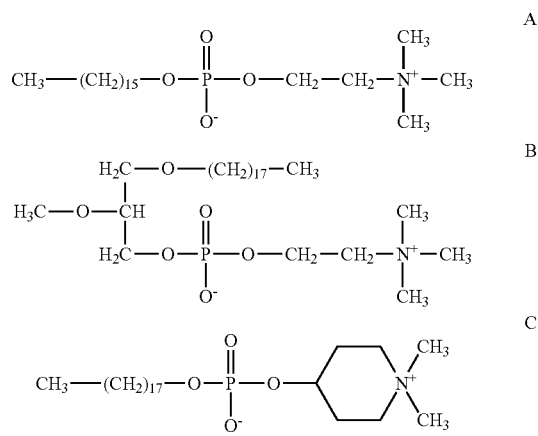

12. HSP90 inhibitors (heat shock protein inhibitors)
    Geldanamycin analogues/derivatives such as 17-AAG and its derivatives, 17-AAG, 17-(Allylamino)-17-demethoxygeldanamycin,

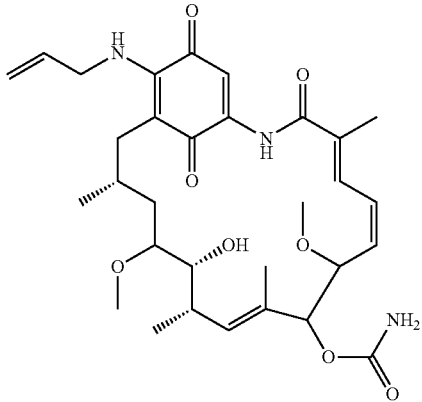 [SMILES: C=CCNC1=C2C[C@@H](C)CC(OC)[C@H](O)[C@@H](C)/C=C(\C)C(OC(N)=O)C(OC)/C=C\C=C(/C)C(=O)NC(=CC1=O)C2=O]

Radicicol and analogues,

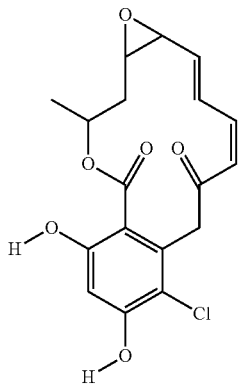 [SMILES: CC1CC2OC2/C=C/C=C\C(=O)Cc2c(Cl)c(O)cc(O)c2C(=O)O1]

Hypericin

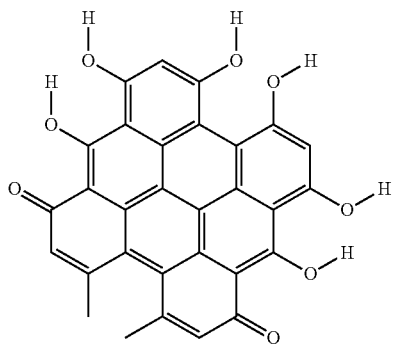 [SMILES: Cc1cc(=O)c2c(O)c3c(O)cc(O)c4c5c(O)cc(O)c6c(O)c7c(=O)cc(C)c8c1c2c(c34)c(c65)c78]

13. Antifungal agents:
    Clotrimazole and analogs,

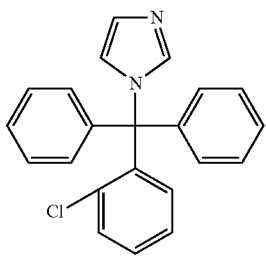 [SMILES: Clc1ccccc1C(c1ccccc1)(c1ccccc1)n1ccnc1]

14. Agents that restore the function of a mutated gene, e.g. agents that suppress non-sense mutations, for example: Gentamicin

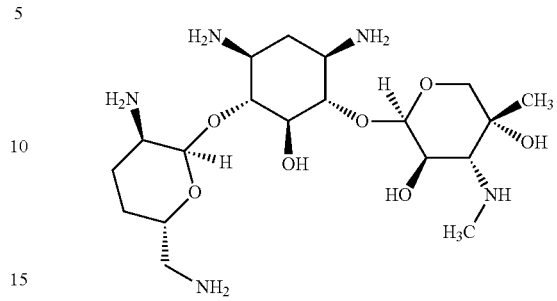

In preparing compositions of this invention one is guided by the teachings of (1) Remingtons Pharmaceutical Sciences, Mack Publishing Co., 17$^{th}$, 18$^{th}$, or 19$^{th}$, Edition, ISBN: 0-912734-04.3, (Also called "Remington: The Science and Practice of Pharmacy"); (2) Pharmaceutics—The Science of Dosage Form Design, Aulton, Churchill Livingston; (3) Appleton and Lange Review of Pharmacy (7$^{th}$ or 8$^{th}$ Ed) by Hall and Reiss, Appleton and Lange; and the like, all of which are incorporated herein by reference. For nanoparticle or liposome delivery, more information is available at http://www.happ1.com/special/mar013.htm and http://www.collabo.com/liposome.htm. Information relating to dendrimer technology is found at http://www.ringer.com/dedrimer/one-.htm.

EXAMPLES

Agents useful to treat neurofibromas in the present invention may be selected by several methods described herein. For example, various compounds/agents described herein as well as other agents that may be selected are tested in cell-based assay for their potency to inhibit cell proliferation of a panel of NF1 related cell lines, are tested to determine an effect on dermal neurofibroma explant assays, and are tested to determine an effect on xenograft models for dermal neurofibromas.

I. In Vitro Assays
1) Cell Proliferation Assays

Several physiologically relevant cells or cell lines were employed to measure compound potency in cell proliferation assays. These cells include: (1) NF1-deficient human malignant peripheral nerve sheath tumor (MPNST) cells, (2) Nf1$^{-/-}$ mouse embryonic Schwann cells, and (3) Nf1- and p53-deficient mouse cell. Mouse Schwann cells are grown on plates coated with laminin and cultured in Dulbecco's Modified Eagle's Medium (DMEM)/Ham's F12 medium (F12), a 1:1 blend of DMEM and F12 media, supplemented with recombinant heregulin-β1 (10 ng/ml), forskolin (2 µM), and N2 supplement (Invitrogen, California. Cat#17502-048). All the other cells are grown in DMEM with 10% fetal bovine serum (FBS). The following publications disclose the preparation of the cell lines used in the cell-proliferation assay.

Basu, T. N., Gutmann, D. H., Fletcher, J. A., Glover, T. W., Collins, F. S., and Downward, J. (1992) *Nature* 356, 713-715

DeClue, J. E., Papageorge, A. G., Fletcher, J. A., Diehl, S. R., Ratner, N., Vass, W. C., and Lowy, D. R. (1992) *Cell* 69, 265-273

DeClue, J. E., Heffelfinger, S., Benvenuto, G., Ling, B., Li, S., Rui, W., Vass, W. C., Viskochil, D., and Ratner, N. (2000) *J Clin Invest* 105, 1233-1241

Vogel, K. S., Klesse, L. J., Velasco-Miguel, S., Meyers, K., Rushing, E. J., and Parada, L. F. (1999) *Science* 286, 2176-2179

Manent, J., Oguievetskaia, K., Bayer, J., Ratner, N., and Giovannini, M. (2003) *J Neurosci Methods* 123, 167-173

Morrissey, T. K., Kleitman, N., and Bunge, R. P. (1991) *J Neurosci* 11, 2433-2442

Verdu, E., Rodriguez, F. J., Gudino-Cabrera, G., Nieto-Sampedro, M., and Navarro, X. (2000) *J Neurosci Methods* 99, 111-117

Kim, H. A., Ling, B., and Ratner, N. (1997) *Mol Cell Biol* 17, 862-872

Zhu, Y., Ghosh, P., Charnay, P., Burns, D. K., and Parada, L. F. (2002) *Science* 296, 920-922

Zhu, Y., Romero, M. I., Ghosh, P., Ye, Z., Charnay, P., Rushing, E. J., Marth, S. D., and Parada, L. F. (2001) *Genes Den* 15, 859-876

Muir, D., Neubauer, D., Lim, I. T., Yachnis, A. T., and Wallace, M. R. (2001) *Am J Pathol* 158, 501-513

Li, Y., Rao, P. K., Wen, R., Song, Y., Muir, D., Wallace, P., van Home, S. J., Tennekoon, G. I., and Kadesch, T. (2004) *Oncogene* 23, 1146-1152

To perform cell proliferation assays, appropriate number of cells that can reach ~70% confluence in 3 days (for example, 3000-6000 cell/well for human MPNST cells and mouse Nf1/p53-deficient cells, 8000-10000 cell/well for mouse embryonic Schwann cell) were plated in 96-well plates. Various concentrations of each compound/agent to be tested were added to the growing media and the cells were then cultured for 3 days. Upon completion of the incubation, media were gently removed and 100 µl of ATPlite solution (Perkin Elmer, Boston, Cat. #6016941) was added in each well. Viable cells were measured by detecting luminescence generated from reaction of ATPlite solution and the ATP in the cells. Potency ranges of various compounds/agents to inhibit cell proliferation of several NF1-related cell lines were determined. The selection criteria for agents/compounds that are useful as good candidates for the local treatment of neurofibromas is based on the selection of any compounds with an IC50s equal or below 10 µM (IC50 is defined as the concentration of an inhibitor that is required for inhibition of cell proliferation by 50%.) Compounds that meet such criteria are: alkylating agents (e.g. Thiotepa), anti-metabolites or nucleoside analogues (e.g. 5-fluorouracil, Sangivamycin, Tubercidin, Triciribine, Cladribine), topoisomerase inhibitors (e.g. Camptothecin, Podophyllotoxin, XK469), microtubule inhibitors (e.g. Mebendazole), selerosing agents (e.g. Bleomycin, Doxycycline and analogues) agents that modulate gene transcription (HDAC inhibitors, such as Tricostatin A), chemopreventative agents (e.g. retinoids such as Fenretinide, retinoic acid and analogues, curcumin and derivatives, EGCG and analogues, and methylglyoxal), kinase inhibitors (e.g. U0126, LY294002, EGFR/ErbB2 inhibitors, KN2941, SU11652, Bay43-9006, rapamycin and their analogues), alkylphospholipids (e.g. miltefosine), HSP90 inhibitors (e.g. Geldanamycin derivatives such as 17-AAG, radicicol and analogues, hypericin), anti-fungal agents (e.g. clotrimazole), agents that suppress non-sense mutations (e.g. gentamicin). In addition, if compounds are believed to have mechanisms of actions that are non-cell autonomous (e.g. immunomodulatory or anti-angiogenesis) or unknown, they may not score as positives but they will be tested in explant models, xenograft models, and in the proof-of-principle clinical trials with NF1 patients if possible.

2) Explant Assay

The efficacy of the compound/agent was tested in an ex vivo tumor explant model as follows. Fresh human dermal neurofibroma was cut into eight small pieces and cultured on standard cell culture plates with medium containing DMEM/F12, 10% FBS, heregulin and forskolin. The pieces were divided into treatment and control groups. Compound at different doses was added to the medium on day 1. No compound was added in the negative control group. All tumor pieces were collected on day 3 and processed for histology by formalin fixation and paraffin embedding. Tissue sections were cut and stained with hematoxylin-eosin for histological analysis. The histological analysis of the paired explant samples was conducted blindly. Three histological parameters were used to score the samples from "−" to "+++": 1) overall tissue integrity; we evaluate tissue integrity by comparing the cellularity of treated samples to the negative control samples. The low cellularity area was defined as >30% less nucleus than the similar area on the control sample. The photograph of each sample at 40× under a bright field microscopy was take using MagnaFire digital camera (Optronics, USA) and stored in computer. The low cellularity areas in the pictures were measured using Photoshop and calculated as Length×Width, and then expressed as a percentage over the total area of the sample. Overall tissue integrity was scored using 0 to 2+ score. In short, good tissue integrity is scored 0 (<5%), 1+ indicates medium tissue integrity (5-25%), 2+ low tissue integrity (>25%). Only 2+ cases were regarded as positive "+" for the final total score; 2) cell death—slides were evaluated by bright field microscopy. At least 100 cells per view were counted. Cell death was scored semi-quantitatively using the 0 to 3+ score. The absence of condensed or fragmented nucleus is scored 0, 1+ indicates the lowest level of detectable cell death (<10%), 2+ moderate cell death (10-20%), and 3+ high cell death (>30%). All 2+ and 3+ cases were regarded as positive "+" for the final total score; and 3) effect on vasculatures.—slides were evaluated by bright field microscopy. The effect on vasculature in treated samples was determined by comparing with the vasculatures in control negative samples. At least 20 vasculatures per sample were counted. Effect on vasculatures was scored semi-quantitatively using the 0 to 3+ score. In short, absence or the lowest level of damaged vasculature is scored 0 (<5%), 1+ indicates of some damaged vasculature (5-25%), 2+ high (>25%). All 1+ and 2+ cases were regarded as positive "+" for the final total score. Final histological score was the sum of the scores of the above three parameters, expressed as "−" to "+++". Any compound with a histological score of "+" or more will be potential good candidates for local treatment of neurofibromas. Compounds that meet such criteria are: alkylating agents (e.g. Thiotepa, Carboplatin), anti-metabolites or nucleoside analogues (e.g. 5-fluorouracil, Sangivamycin, Tubercidin), topoisomerase inhibitors (e.g. Podophyllotoxin), microtubule inhibitors (e.g. Mebendazole), sclerosing agents (e.g. Bleomycin), anti-inflammatory agents or nonsteroidal anti-inflammatory agents (NSAIDs) (e.g. Diclofenac), agents that modulate gene transcription (HDAC inhibitors, such as Tricostatin A, Valproic acid), chemopreventative agents (e.g. retinoids such as Fenretinide), HSP90 inhibitors (e.g. Geldanamycin derivatives such as 17-AAG, radicicol and analogues).

3) Xenograft Assay

The efficacy of the compound was tested in a tumor burden reduction study in a mouse dermal neurofiberoma (DNF) xenograft model as follows. Female SCID mice between 5 and 6 weeks of age and weighing approximately 20 g were obtained from Charles River Laboratories (Wilmington, Mass.). Animals were implanted subcutaneously with fragments of fresh human DNF. 3 days following inoculation, the animals were randomly allocated into treatment and control groups. Each group contained 6 tumored mice. Each mouse was ear-tagged and followed individually throughout the experiment. Dosing started on Day 1 following randomization. The compound was administered intralesionally on a twice weekly schedule for 4 weeks. Compound plus vehicle was administered at different doses in the volume of 50 μl. Vehicle alone was administered to serve as the negative control. Mice were weighed twice weekly, and tumor measurements were obtained using calipers twice weekly, starting on Day 1. Tumor volumes were calculated by the standard formula $(W^2 \times L)/2$, where L is the length and W is the width. (Blaskovich M A, Lin Q, Delarue F L, Sun J, Park H S, Coppola D, Hamilton A D, Sebti S M (2000), Design of GFB-111, a platelet-derived growth factor binding molecule with antiangiogenic and anticancer activity against human tumors in mice. *Nat Biotechnol* 18: 1065-1070). The tumor fragments were weighed before inoculation and after sacrifice. The differences were expressed as the percentage of original tumor weight. The harvested tumors were processed for histology by formalin fixation and paraffin embedding. Tissue sections were cut and stained with hematoxylin-eosin for histological analysis. The effect of the compound on xenografts was determined by either of: 1) tumor weight measurements—the tumor weight differences before and after treatment in both treated and control groups were analyzed using Student's t test. The result of a certain dose of the compound is considered to be "+" when the difference in tumor weight is statistically significant ($p<0.05$). 2) histological analysis—three histological parameters were used to score the samples. A) tissue necrosis—the picture of each sample at 40× under a bright field microscopy was take using MagnaFire digital camera (Optronics, USA) and stored in computer. The necrosis areas in the pictures were measured using Photoshop and calculated as Lenth×Width, and then expressed as a percentage over the total area of the sample. Overall tissue necrosis was scored using 0 to 2+ score. In short, absence of necrosis is scored 0 (<5%), 1+ indicates medium tissue necrosis (5-25%), 2+ high tissue necrosis (>25%). Only 2+ cases were regarded as positive "+" for the final total score. B) tissue cellularity—the low cellularity area in the treated samples was defined as >30% less nucleus than the similar area on the control sample. The picture of each sample at 40× under a bright field microscopy was take using MagnaFire digital camera (Optronics, USA) and stored in computer. The low cellularity areas in the pictures were measured using Photoshop and calculated as Length×Width, and then expressed as a percentage over the total area of the sample. Overall tissue integrity was scored using 0 to 2+ score. In short, good tissue integrity is scored 0 (<5%), 1+ indicates medium tissue integrity (5-25%), 2+ low tissue integrity (>25%). All 1+ and 2+ cases were regarded as positive "+" for the final total score. C) inflammatory cells infiltration—slides were evaluated by bright field microscopy. At least 100 cells per view were counted and the number of inflammatory cells per 100 total cells was calculated as a percentage for each sample. Inflammatory cells infiltration was determined by the difference between the percentage of the treated samples with that of the control sample and scored semi-quantitatively using the 0 to 3+ score. In short, absence of or very low difference in inflammatory cells infiltration is scored 0 (<5%), 1+ indicates medium level of Inflammatory cells infiltration (5-25%), and 2+ high level of inflammatory cells infiltration (>25%). All 1+ and 2+ cases were regarded as positive "+" for the final total score. Final histological score was the sum of the scores of the above three parameters, expressed as "−" to "+++". Any compound with either a "+" in tumor weight measurement or a histological score of "+" or more will be potential good candidates for local treatment of neurofibromas. Compounds that meet such criteria are: alkylating agents (e.g. Thiotepa, Carboplatin), anti-metabolites or nucleoside analogues (e.g. 5-fluorouracil, Sangivamycin, Tubercidin), topoisomerase inhibitors (e.g. Podophyllotoxin), microtubule inhibitors (e.g. Mebendazole), sclerosing agents (e.g. Bleomycin, Doxycycline), anti-inflammatory agents or nonsteroidal anti-inflammatory agents (NSAID) (e.g. Diclofenac), agents that modulate gene transcription (HDAC inhibitors, such as Tricostatin A, Valproic acid), chemopreventative agents (e.g. retinoids such as Fenretinide), alkylphospholipids (e.g. miltefosine), HSP90 inhibitors (e.g. Geldanamycin derivatives such as 17-AAG, radicicol and analogues).

The compounds/agents above were tested using one or more of the above assays to select agents useful in the present invention to treat neurofibromas: The assays are preferably run in a particular order and when "positive results" are obtained, then the next assay is performed and so on. For example if an agent is tested in the cell proliferation assay and is positive by the criteria disclosed above, then this agent is tested in the explant assay, and if positive according to the above criteria, then this agent is tested in the xenograft assay. If all three of the assays results in positive results based on the criteria for a specific agent or compound, then this agent expected to be a good candidate for successful treatment of neurofibromas, specifically NFL). In addition, for compounds that are believed to have mechanisms of actions that are non-cell autonomous (e.g. immunomodulatory or anti-angiogenesis) or unknown, they are expected to be good candidates for successful treatment of neurofibromas if positive results are obtained in xenograft models, or in the proof-of-principle clinical trials with NF1 patients if possible.

II. In Vivo Studies

General Study Design for Local Treatment of Neurofibromas with an Agent or Compound A. Intralesional Administration The study was a proof-of-concept, prospective, safety and efficacy study of the effect of intralesionally administered drugs given once a week to 3 target cutaneous neurofibromas for 4 consecutive weeks. Six subjects were enrolled. All subjects had the diagnosis of NF1 and possessed at least 6 cutaneous neurofibromas 0.5 to 1.5 cm, inclusive, on the back. All subjects were from 18 to 65 years of age, inclusive. All subjects otherwise were in good health, or had stable concomitant medical conditions appropriately managed by a primary care physician. Enrolled subjects demonstrated no clinically significant abnormalities on both laboratory and physical examination, other than the features of NF1. After screening and enrollment, all subjects received a defined volume (based on the size of the lesion) of intralesional drug once weekly into 3 target cutaneous neurofibromas that are 0.5 to 1.5 cm in diameter, inclusive, in its largest dimension. Each target cutaneous neurofibroma was different in size, with one 0.5 to 0.8 cm in diameter, a second between 0.81 to 1.2 cm in diameter, and a third 1.21 to 1.5 cm in diameter. Concomitantly, three control cutaneous neurofibromas found on the torso and/or appendages of the same range in sizes received sterile normal saline. All lesions prior to injection were locally anesthetized with lidocaine 1% and epinephrine 1:100,000. During the study period, subjects received 4 weekly intralesional injections at the 6 lesions (the 3 target lesions receiving drug, the 3 control lesions receiving normal saline), and were followed every week during receipt of the study medication and three weeks after the last dose had been administered. At every visit, subjects underwent physical examinations, recording of adverse events and concomitant medications, and measurement and photography of both the target and control lesions. Assessment included the exact measured dimensions (in two axes) of the two assessed lesions. Photography entailed standardized digital images of both the target and control lesions (accompanied by a ruler) without any identifying features of the subject represented. For each subject, photography involved consistent focal length, lighting, and angle of exposure carried over from visit to visit. On each visit, each subject was questioned for potential side effects of the receipt of the study medication either during its administration or in between visits, including pain, pruritus, irritation, discoloration, ulceration, or any other new sign or symptom—either local or distant from the target and control lesions—not present at baseline.

In one of the local injection studies, in which doxycycline was the study drug, 89% of the tumors injected with doxycycline showed either partial or complete elimination of the dermal neurofibroma while all of the controls showed no change. Similarly, in another study using dichlofenac as the study drug, 48% of the tumors injected with diclofenac showed partial or complete elimination of the dermal neurofibroma while all of the controls showed no change.

B. Topical Administration

The subjects with neurofibromas are selected as described above in A, and similar controls are run with untreated neurofibromas on the same subject. Alternative methods of administration include topical application by applying a composition containing any one or more of the agents described herein, in combination with 5% gel in sufficient quantities to the skin covering a neurofibroma to cover the tumor once a day for 21 days. Additionally, topical application is performed by applying a dermabrasion device in which the device's micro-needles are coated with the composition comprising the agent to the skin covering the tumor once a day for 7 days.

We claim:

1. A method of treating a dermal neurofibroma, a subdermal neurofibroma, or a superficial plexiform neurofibroma in a subject in need of such treatment, which method comprises locally administering a composition to the region of the tumor, wherein the composition comprises (a) one non-carcinogenic agent for treating the neurofibroma on the subject, and optionally (b) a pharmaceutically acceptable excipient that aids in transporting the non-carcinogenic agent into the tumor where it is preferably maintained for a sufficient period of time to treat the neurofibroma; wherein the non-carcinogenic agent is a non-steroidal anti-inflammatory (NSAID) agent.

2. The method of claim 1, wherein said local administration is topically applying said composition to the surface of the skin in the region of the tumor, and wherein said excipient aids in transporting the agent across the skin and to the tumor and preferably maintains the agent on the skin of the subject.

3. The method of claim 1, wherein said local administration is intralesionally injecting said composition into the tumor.

4. The method of claim 1, wherein the excipient includes a skin penetrant.

5. The method of claim 1, wherein the NSAID is diclofenac.

* * * * *